(12) United States Patent
Knuebel et al.

(10) Patent No.: US 12,243,643 B2
(45) Date of Patent: Mar. 4, 2025

(54) DETERMINING EXTERNAL HAIR DAMAGE

(71) Applicant: Henkel AG & Co. KGaA, Duesseldorf (DE)

(72) Inventors: Hans Georg Knuebel, Duesseldorf (DE); Erik Schulze Zur Wiesche, Bielefeld (DE)

(73) Assignee: HENKEL AG & CO. KGAA, Duesseldorf, NY (US)

(*) Notice: Subject to any disclaimer, the term of this patent is extended or adjusted under 35 U.S.C. 154(b) by 973 days.

(21) Appl. No.: 17/055,280

(22) PCT Filed: Apr. 29, 2019

(86) PCT No.: PCT/EP2019/060853
§ 371 (c)(1),
(2) Date: Nov. 13, 2020

(87) PCT Pub. No.: WO2019/219355
PCT Pub. Date: Nov. 21, 2019

(65) Prior Publication Data
US 2021/0121123 A1    Apr. 29, 2021

(30) Foreign Application Priority Data
May 16, 2018    (DE) ................. 10 2018 207 558.1

(51) Int. Cl.
*G01N 33/48* (2006.01)
*A45D 44/00* (2006.01)
(Continued)

(52) U.S. Cl.
CPC ........... *G16H 50/20* (2018.01); *A45D 44/005* (2013.01); *A61B 5/0077* (2013.01); *A61B 5/448* (2013.01);
(Continued)

(58) Field of Classification Search
CPC ...... G16H 50/20; G16H 20/10; A45D 44/005; A45D 2044/007; A61B 5/0077;
(Continued)

(56) References Cited

U.S. PATENT DOCUMENTS

2009/0132450 A1* 5/2009 Schlottmann ............ G06N 3/02
706/46
2015/0107616 A1* 4/2015 Bormashenko ......... D06P 3/305
132/201
(Continued)

FOREIGN PATENT DOCUMENTS

DE    102016225674 A1    7/2017
DE    102016208631 A1    11/2017
(Continued)

OTHER PUBLICATIONS

English machine translation of DE 102016225674 A1 obtained from ip.com on Nov. 18, 2023.*
(Continued)

*Primary Examiner* — Russell S Negin
(74) *Attorney, Agent, or Firm* — Lorenz & Kopf, LLP

(57) ABSTRACT

An arrangement for determining external damage to hair is given. A device comprising: a reading unit adapted to obtain optical characteristics of hair; and a processing unit adapted to receive the optical characteristics from the reading unit and to determine surface properties of the hair from the optical characteristics, wherein the processing unit implements a pattern recognition algorithm and is adapted to assign, by employing the pattern recognition algorithm, the surface properties to a predetermined damage including at least one damage type and an associated damage level and to output the damage.

13 Claims, 3 Drawing Sheets

(51) Int. Cl.
*A61B 5/00* (2006.01)
*G01N 33/50* (2006.01)
*G06F 18/24* (2023.01)
*G06N 3/08* (2023.01)
*G16H 20/10* (2018.01)
*G16H 50/20* (2018.01)

(52) U.S. Cl.
CPC .............. *G06F 18/24* (2023.01); *G06N 3/08* (2013.01); *G16H 20/10* (2018.01); *A45D 2044/007* (2013.01); *A61B 5/7267* (2013.01); *A61B 2576/02* (2013.01)

(58) Field of Classification Search
CPC ..... A61B 5/448; A61B 2576/02; G06F 18/24; G06N 3/08
See application file for complete search history.

(56) References Cited

U.S. PATENT DOCUMENTS

| | | |
|---|---|---|
| 2017/0038297 A1 | 2/2017 | Miklatzky et al. |
| 2019/0285546 A1 | 9/2019 | Knuebel et al. |
| 2019/0350515 A1 | 11/2019 | Mueller et al. |

FOREIGN PATENT DOCUMENTS

| | | | |
|---|---|---|---|
| JP | 4071891 B2 | 4/2008 | |
| WO | WO-2017153262 A1 * | 9/2017 | ............. A61B 5/448 |

OTHER PUBLICATIONS

EPO, International Search Report issued in International Application No. PCT/EP2019/060853, dated Jul. 8, 2019.

Egmont-Petersen, et al.: "Image processing with neural networks—a review", Pattern Recognition, Pergamon GB, vol. 35, 2002, pp. 2279-2301.

Anonymous: "Pattern recognition—Wikipedia, the free encyclopedia", 2015, retrieved from the internet: https://en.wikipedia.org/w/index.php?title=Pattern.

* cited by examiner

DETERMINING EXTERNAL HAIR DAMAGE

CROSS-REFERENCE TO RELATED APPLICATION

This application is a U.S. National-Stage entry under 35 U.S.C. § 371 based on International Application No. PCT/EP2019/060853, filed Apr. 29, 2019, which was published under PCT Article 21(2) and which claims priority to German Application No. 10 2018 207 558.1, filed May 16, 2018, which are all hereby incorporated in their entirety by reference.

TECHNICAL FIELD

The present disclosure relates to an arrangement for determining external damage to hair, a computer program product which is designed to be executed on a computing unit, and a method for determining external damage to hair.

BACKGROUND

When hair is treated with cosmetic products, the effect of the product, e.g. the intensity of a coloring, can depend very much on the damage to the hair. The damage or loss may denote a type of damage (which damage) and a degree of damage (extent of damage,) but may also refer to several different types of damage and associated degrees of damage. Damaged hair is often difficult to handle and lacks shine.

There are many different hair treatment products on the market which are designed to improve different hair properties or parameters, such as shine. In many cases, however, the user of such products does not know to what extent (degree of damage) and in what way (type of damage) his hair is damaged. This can lead to the user resorting to products that are less suitable in his case and being dissatisfied with their effectiveness after use.

That is why it can be important to identify any damage to the hair.

Hair can be damaged by natural or artificial processes. The natural processes can, for example, have a combined (e.g. simultaneous) effect of UV light and oxygen (02) on the hair. The artificially induced processes may include, for example, the application of hair dyes (also known as coloring), bleaching, and/or the creation of a permanent wave.

In addition to desired cosmetic effects, such as a lightening of the hair, this can also cause severe damage to the hair, for example when using oxidizing agents.

The damaging process can be caused by an oxidation of amino acids, for example an oxidation of the amino acids cystine and cysteine, which are common in hair, to cysteic acid. Cystine can form intermolecular disulfide bridges (also known as S-S bridges) in the hair, so cystine is extremely important for the mechanical stability of the hair.

The oxidation of these bridges to cysteic acid can destroy the mechanical stability of the hair and even lead to complete hair breakage if used several times. However, macroscopically perceptible, e.g. tactile, properties of the hair, such as surface roughness, can be negatively influenced. The results of cosmetic treatments, especially damaging procedures, can also be massively changed at an early stage of damage compared to the results with undamaged hair.

More and more product users want a product tailored to their individual needs. This applies to beauty products such as skin and/or hair treatment products.

It can be regarded as the task of the present disclosure to enable the determination of external damage to hair in a simple way and to issue a hair treatment instruction adapted to this.

This task is solved with the independent claims. Further developments of the present disclosure result from the dependent claims and from the following description.

BRIEF SUMMARY

Methods, arrangements, and a computer for determining external damage to hair are provided. In an exemplary embodiment, an arrangement includes a reading unit designed to obtain optical features of hair. A processing unit is designed to receive the optical features from the reading unit and to determine surface properties of the hair from the optical features. The processing unit implements a pattern recognition algorithm and is adapted to assign the surface properties to a predetermined damage, where the damage includes at least one damage type and an associated damage level, The damage is then output.

A computer for determining external damage to hair is provided in another embodiment. The computer includes a program configured to receive optical characteristics of hair, and determine surface properties of the hair based on the optical characteristics. The program is also configured to determine a damage of surface properties by employing a pattern recognition algorithm that is based on predetermined damages including at least one damage type and an associated damage level. The program is further configured to output the damage.

A method of determining external damage to hair is provided in yet another embodiment. The method includes receiving optical characteristics of hair, and determining surface properties of the hair based on the optical characteristics. Damage to the surface properties is determined by employing a pattern recognition algorithm that is based on predetermined damages including a damage type and an associated damage level. The damage is then output.

BRIEF DESCRIPTION OF THE DRAWINGS

The present disclosure will hereinafter be described in conjunction with the following drawing figures, wherein like numerals denote like elements, and wherein.

DETAILED DESCRIPTION

Figure 1:
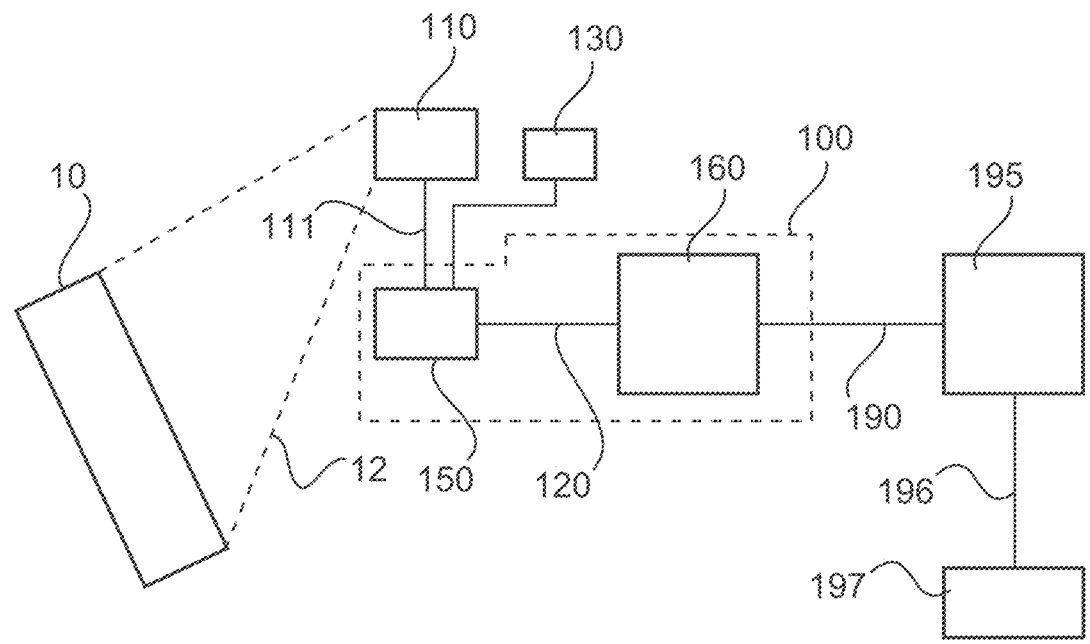
FIG. 1 is a schematic representation of an arrangement for detecting external damage to hair according to an execution example.

The following detailed description is merely exemplary in nature and is not intended to limit the disclosure or the application and uses of the subject matter as described herein. Furthermore, there is no intention to be bound by any theory presented in the preceding background or the following detailed description.

The present disclosure is based, inter alia, on the following findings: The development of personalized hair cosmetic products is made possible by a comprehensive characterization of a person's hair condition so that effective individualized product recommendations can be made, e.g. for hair care products. The characterization can basically be done by the person himself, in a hairdressing salon by a hairdresser or at a point of sale of hair treatment products. For all variants, simple, inexpensive, and robust procedures are helpful and sometimes required. The determination of external and internal hair damage is in principle possible with a variety of biophysical measuring methods. However, many of these processes are extremely complex in terms of equipment and cannot be used by end users. All mechanical processes are very demanding so that the relevant mechanical data can be determined with the necessary precision. In addition, these methods require a considerable amount of calibration, maintenance, and cleaning. Therefore, there is a great demand for non-mechanical, ideally non-contact methods for hair analysis.

It has now been found that the question of whether a hair or a hair sample is damaged or undamaged (a further subdivision on a scale with degrees of damage with more than two levels is also possible) can be answered without much effort with the help of machine-supported learning methods, for example using "deep learning" techniques. This allows the isolated quantification of the morphological damage on the surface of a hair, without recording the properties of the entire hair.

According to one aspect, an arrangement for determining external damage to hair is given. The arrangement has a reading unit and a processing unit. The reading unit is designed to obtain optical characteristics of hair. The processing unit is designed to receive the optical characteristics from the reading unit and to determine surface properties of the hair from the optical characteristics. The processing unit implements a pattern recognition algorithm and is designed to assign, by employing the pattern recognition algorithm, the surface properties to a predetermined damage including at least one damage type and an associated damage degree and to output the damage.

Optical characteristics of hair are understood as optically detectable features, for example those features which can be seen in an image recording in the visible light spectrum. In particular, the optical characteristics concern surface features, such as the structure of the cuticle, which is the outer layer of a hair and can also be described as the cuticle layer. If reference is made to the hair surface in this description, this is equivalent to the outer surface of the cuticle.

The reading unit receives the optical features, for example, from an optical detection unit or from a data memory or retrieves the optical features in the form of image information from the optical detection unit or the data memory.

The reading unit can be designed as an access interface, which connects an image source (optical acquisition unit or data storage) or couples the image source communicatively with the processing unit.

The processing unit determines the surface properties of the hair based on the optical characteristics or images of hair. For this purpose, the processing unit can implement an image processing algorithm that extracts the structure of the hair surface from a line in an image of the hair surface. For example, the processing unit can determine the shape of individual cuticle cells or scales. Individual cuticle cells are recognized in an image recording based on a line pattern on the hair surface.

The processing unit applies a pattern recognition algorithm to detect the shape of the cuticle cells and to determine the external damage of a hair, for example by comparing the detected surface properties with previously known and stored damage to hairs and assigning them to a damage.

A damage can refer to a type of damage and an associated extent or degree of damage. The following aspects are some of the possible types of damage: Shape of the edges of the cuticle cells (round, frayed); protruding cuticles, e.g. cuticle cells detached or protruding from the cortex of the hair at the edges; length of the exposed cuticle cells; distances between the edges of the cuticle cells; holes and/or bubbles in the surface or individual cuticle cells; surface roughness (e.g. elevations and/or depressions in the surface); deposits on the cuticle; and visibility of the endocuticle.

For each of these types of damage, an extent or degree of damage can be specified. Different shapes of edges of cuticle cells can be assigned to a degree of damage, so that an image of a hair is assigned to the most visually similar degree of damage. In this way, the degree of damage regarding the edges can be easily assigned.

In general, external damage in the sense of this description can be damage to the cuticle of hair with a damage depth of from about 1 to about 5 µm. The damage may be a change in the appearance of the surface of the cuticle and may particularly affect the shape, type, length, number and/or spacing of indentations in the cuticle.

The same approach is used for the other types of damage. The processing unit matches the surface properties of an examined hair with predetermined damage and determines the damage of the hair sample based on this match.

However, the pattern recognition algorithm cannot only be based on image matching and similarity detection. For example, an artificial neural network can also be used for pattern recognition, which does not determine the damage by comparison with known recordings but based on the configuration of the artificial neural network. For this purpose, the neural network can go through a configuration phase in which different image recordings of hair samples are fed to it, each with a fixed or predefined damage. In this way, the neural network learns to recognize damage from image recordings without comparing a hair sample image recording with other image recordings.

Through pattern recognition, a hair sample can be assigned to a damage category. Damage categories can be a numerical value that indicates how badly the hair is externally damaged and/or what type of damage it is. The numerical value can contain several digits, of which the position is assigned to the type of damage and the value of the digit indicates the degree of damage. For example, the number "0-2-1-3-4-2" could indicate that the shape of the edges of the cuticle cells (first digit) is inconspicuous or indicates no damage (value 0), the cuticle cells at the edges are detached from the cortex of the hair (second digit, value 2), the length of the exposed cuticle cells indicates minor damage (third digit, value 1), the distances between the edges of the cuticle cells (fourth digit) indicate a high degree of damage (value 3), holes and/or bubbles are strongly present in the surface or individual cuticle cells (fifth digit) (value 4), and deposits on the cuticle and visibility of the endocuticle (sixth digit) are also slightly present (value 2). Each individual digit can indicate up to ten different degrees of damage, namely from 0 to about 9. It is also conceivable to further subdivide the scale and use two-digit or multi-digit numbers for each type of damage. However, the limits of such a division of the scale lie in the question of how exactly the damage can be detected and how useful a division into many degrees is. Typically, a subdivision into two to four degrees of damage can be sufficient to distinguish between no damage, light damage, above average damage, or severe damage.

The type and degree of damage is not determined solely on the basis of an image acquisition, but by using known hair samples with associated damage, either by comparing the hair sample with the already classified image acquisitions or by feeding the image acquisition of the hair sample to an artificial neural network, which assigns damage to the hair sample based on its configuration.

This makes it possible to determine a morphological damage on the surface of a hair without making any statements about the inner condition of the hair. For certain hair treatments, the inner condition of the hair may be irrelevant or negligible. Procedures that record the inner condition of the hair may therefore give a misleading value for the damage to the hair for some treatments. This is prevented in the present case by using the bare outer morphological condition.

An image recording of a hair sample preferably contains a single hair. It is also possible to take several images of different hairs from one person to get a meaningful statement about the average condition of the hair. An image of a hair typically shows the entire thickness or diameter of a hair and extends over a section of the hair's length. The longitudinal section of the hair contained in the image capture can roughly correspond to the thickness of the hair, i.e. between a few hundredths of a millimeter and a few tenths of a millimeter, e.g. between about 0.04 mm and about 0.15 mm.

The image capture of the hair sample is preferably in the same resolution as the image captures used to configure the pattern recognition algorithm. Preferably, images of all hair samples are taken in the same resolution and fed into the processing unit.

According to one design, the pattern recognition algorithm is an artificial neural network comprising an input layer, at least one hidden layer, and an output layer, wherein the neural network is designed to output the damage based on the surface properties.

It may be intended to apply the approaches of "deep learning" to the artificial neural network. The neural network can have a high depth, which is associated with a high number of hidden layers. Each layer has a plurality of so-called artificial neurons.

The neural network is configured so that an image of a hair sample is fed to the input layer, the neurons of the input layer interact with the neurons of the hidden layers, whereby different hidden layers interact with each other, and the output layer indicates the damage of the hair sample.

According to a further embodiment, the processing unit is designed to operate the pattern recognition algorithm in a configuration mode, wherein the processing unit is designed to supply the pattern recognition algorithm in the configuration mode with optical features of a plurality of hairs with different damage and to query and assign damage for each individual hair and its optical features.

This configuration mode can also be called learning mode or training mode of the neural network. Here, the neural network is made familiar with different types and degrees of damage and the neurons are interconnected accordingly by the neural network in order to be able to determine and output the damage for a new and unknown image acquisition of a hair sample.

According to another design, the reading unit is designed to obtain the optical characteristics from an optical detection unit.

The reading unit can be directly coupled with an optical acquisition unit for communication. The optical acquisition unit can be a camera or other device to create an image of a hair sample.

According to another design, the optical acquisition unit is a microscope which has a magnification of at least about 100 times, preferably at least about 500 times, more preferably at least about 1000 times and even more preferably at least about 2000 times.

Starting from a hair diameter between about 0.04 mm and about 0.12 mm, a hair is enlarged at about 1000× magnification to a thickness of about 40 mm to about 120 mm as shown in the image, which makes it possible to recognize individual cuticle cells or scales and their edges.

According to another version, the reading unit is designed to obtain the optical characteristics from image recordings of hair.

The lines contained in the captured image can be used to determine the structure of the hair surface. This structure is the basis for assigning a damage. The image recordings can be in a digital data format.

According to another version, the reading unit is designed to read the captured image from a digital data memory.

For example, images from a hair sample are stored on a portable digital data storage medium such as an SD card, USB storage medium, floppy disk, CD-ROM or DVD and can thus be sent to a remote location where the image recordings are fed through the array for analysis. Alternatively, the image recordings can be stored on a hard disk in a computer and made available for further processing.

It is possible that the images are transferred to the processing unit via a data transmission link, either directly from the optical acquisition unit to the reading unit or to the processing unit, or from the data memory or the computer on which the images are stored.

The optical acquisition unit may have an interface through which a connection to the reading unit or the processing unit is established. This connection is designed to transmit information in at least one direction, although bidirectional communication is also possible. Image data is transferred from the optical acquisition unit to the processing unit and, for example, control commands from the processing unit to the optical acquisition unit. The connection can be wired or wireless. Wired connections can, for example, use optical or electrical signals to transmit information. Wireless connections typically use electromagnetic waves for signal transmission, e.g. radio signals or even optical signals.

For the connection of the optical acquisition unit to the reading unit or computing unit protocols can be used, which work according to the principles of meshed networks. For example, the thread protocol, which is based on IPv6, can be used for data transmission and for connecting the optical acquisition unit to the reading unit or processing unit. The thread protocol is used to connect automated or partially automated devices with each other, in this case for example the optical acquisition unit with the reading unit or processing unit.

The optical detection unit and the other elements of the arrangement can be in the same room or spatially separated from each other (for example in separate buildings). In case the image data is transferred from the acquisition unit to the reading unit or the processing unit, only a data transmission link between these elements is required, as described above.

According to another version, the arrangement has an evaluation unit, whereby the evaluation unit is designed to compare characteristics of treatment products for the treatment of hair with the damage of an examined hair sample and to determine an effect of the treatment products on the hair in consideration of the determined damage.

The treatment of hair is of course a non-therapeutic treatment.

The treatment agent is thus selected depending on the determined damage and output by the evaluation unit.

According to another version, the evaluation unit is designed to receive information from a treatment agent data memory about the treatment of hair according to the determined damage and to output the information received.

The evaluation unit can be designed as a processor or a computer. It is also conceivable that the evaluation unit is a software module that runs on or is executed by a processor and performs the above-mentioned functions. The software module of the evaluation unit can be executed on the same or a different processor as the functions of the processing unit.

The evaluation unit can transmit the received messages to an optical or acoustic output unit, so that the messages are provided by the output unit to a human user or operator. The acoustic output unit can be a speaker, and the optical output unit can be a monitor or a display.

These instructions for the treatment of hair can be general instructions (without reference to a specific treatment product) concerning the treatment of hair, but they can also be instructions with reference to a specific treatment product. The hints may also include explanations of which behavior affects which properties of the hair and how.

The treatment product data memory may contain information from studies and information from literature sources and/or scientific publications. The evaluation unit can be designed to output an extract of this information to a user, or at least point out the information to the user, depending on the captured properties of the hair.

According to another version, the evaluation unit is designed to request information from a user and to additionally consider this information when requesting the treatment agent data memory in order to obtain from the treatment agent data memory characteristics of treatment agents for the treatment of hair according to the requested information.

The information requested can be collected by employing a predefined questionnaire, in which a statement by the user is given weight or is selected from one of several possible answers. The prescribed questionnaire can deal in particular with the user's habits and extraordinary stresses and strains, e.g. dietary habits, duration and quality of sleep, amount drunk, type of drinks, use of stimulants (e.g. nicotine, alcohol), professional and leisure activities (spending a lot of time outside buildings in all weathers, staying in the mountains, visiting a solarium). The age, gender and ethnicity of the user can also be queried and used to query the treatment agent data store. The requested information can also relate to a desired or achievable property of the hair and thus specify a target or desired state.

The information can be entered via an input unit. The input unit can be connected to the evaluation unit by employing signals. The input can be done via a touch screen, for example, where the user is presented with statements or questions to which an answer of the user is assigned.

However, the statements provided by the user can also be made available to the processing unit by other techniques. For example, this user information can be transmitted together with the images of the hair sample.

The evaluation unit can create a user profile and save the hair sample and the corresponding statements or information of the user. This makes it possible to compare later hair samples with earlier hair samples and to observe and evaluate changes in the damage over time.

According to another version, the evaluation unit is designed to output information about a treatment agent, e.g. a product name, information about ingredients and/or composition of a treatment agent and/or application instructions for hair treatment.

This enables a user to form his or her own opinion about a treatment product in its entirety. In addition, the user can be given instructions for use related to a treatment product or independently of it. The application instructions can refer to desired and/or undesired behavior.

According to another version, the evaluation unit is designed to receive an input from a user after the output of characteristics of a treatment agent and/or application instructions and to initiate an action concerning the output treatment agent and/or the output application instructions based on this input.

The action may, for example, relate to the user being offered a treatment product for sale and the user being able to initiate the purchase by employing an input. In addition to the purchase of treatment products, the user can also be offered more detailed information on the purchase. This more detailed information may refer to more detailed treatment and application instructions. For example, the program receives the request that the user wishes to purchase the treatment product, stores the request and/or transmits the request to a commercial company that distributes the treatment products. The user is requested by the computer program to enter his personal data (address, bank information, shipping preference, etc.) via the input unit.

Alternatively, the user can be directed where, for example in a drugstore, hairdressing salon, pharmacy, etc. in his vicinity, he can purchase the dispensed treatment product locally.

More and more customers want a product individually tailored to their needs. Accordingly, the user can be recommended an individually manufactured treatment product and an order process can be initiated, for example by calling up the website of a manufacturer of individual hair treatment products.

This may be a treatment product specially manufactured for one user or a so-called "mass customized" product. In the case of a "mass customized" product, individualization can be achieved by varying a few features of a product that are decisive from the customer's point of view. These "mass customized" products are preferably based on the concept of modularization, i.e. the product can be individually assembled from various modules/components.

There are often numerous interdependencies between the many different characteristics/ingredients of a product, which can be expressed as "commandments" or "prohibitions". To obtain a clear product definition, it can be advantageous to use a product configurator during the ordering process. This configurator helps the user to select the features/ingredients and draws his attention to the allowable/non-permissible combinations of features, the latter of which cannot then be selected.

In the case of hair treatment products, the relevant product characteristics include the chemical ingredients of the products, the physical properties of the products and the way in which the products are packaged. With the help of a product configurator, for example, the selection of chemically and/or physically incompatible ingredients or the selection for the determined degree of damage/strain/etc. of unsuitable ingredients can be avoided. Conversely, the selection for the determined degree of damage/strain/etc. of suitable ingredients can be specified or suggested by the product configurator.

It is also possible to produce an individual hair treatment product on site, i.e. for example in a hairdressing salon or at a point of sale of hair treatment products, such as a drugstore, using a mixing device, preferably a smart mixer.

According to another aspect a computer program product is specified, which is designed to be executed on a computing unit. The computer program product is designed to instruct a processor of the computing unit to perform the following steps when the computer program product is executed on the computing unit: Receiving optical features of hair; determining surface properties of the hair based on the optical features; determining a damage of the surface properties by employing a pattern recognition algorithm that is based on predetermined damages including at least one damage type and an associated damage degree; and outputting the damage.

The computer program product allows the control and follow-up of the results by displaying (e.g. graphically) the measurement results over time. Based on the results obtained, the computer program product provides individual treatment and product tips. The quality of the treatment and product tips can be improved by the user answering additional questions about his hair condition, dietary habits, general health, and other behavior that the computer program product can process accordingly. This is based not only on e.g. literature data, but also on the treatment success of other users of the computer program product, especially treatment successes of other users who have at least a similar hair condition.

The data collected through the questionnaire can be used to analyze a development of the condition of the user's hair under the given circumstances, i.e. the data entered by the user. This development can be compared with the development of other users. From this, it can be concluded whether, during treatment with a given product, the evolution of users with similar or identical submissions in the questionnaire is similar or different from users with different submissions.

For example, it is possible to draw conclusions about the influence of a certain fact on the success of the treatment. If, for example, the development of one type of damage in several smoking persons with a specific cigarette consumption (e.g. ten cigarettes per day) shows a significant deviation from the development of the same type of damage in non-smokers, it can be concluded that smoking affects the specific parameter in a way that can be quantified. Alternatively, it can be concluded that a different product or treatment is recommended for smokers.

The data entered by the user can thus be used for a global analysis in order to monitor the success of a treatment and the effectiveness of a product under different conditions and, if necessary, recommend changes to the treatment and/or product.

According to another aspect, a method for determining external damage of hair is given. The procedure has the following steps: Receiving optical features of hair; determining surface properties of the hair based on the optical features; determining a damage of the surface properties by employing a pattern recognition algorithm that is based on predetermined damages including at least one damage type and an associated damage degree; and outputting the damage.

According to an execution form, the procedure also has the following step: Configure the pattern recognition algorithm based on many hairs with different damage, whereby a damage is queried and assigned for each individual hair. This step can be performed before unknown hair samples are fed to the processing unit for external damage detection. However, it is also conceivable that a dedicated configuration can be dispensed with, for example if the pattern recognition algorithm is already configured.

This provides a non-mechanical, non-contact method for determining the external damage of hair. The method is based on enlarged optical images of hair samples, which are linked to approaches of machine-supported learning or pattern recognition.

According to another aspect, a procedure for determining a treatment agent is given. This procedure is based on the external damage of hair determined according to the above procedure and has the following steps: Using the specific external damage of hair; and determining a treatment agent whose properties are associated with the external damage and which has a desired effect on the external damage.

The treatment agent is selected or determined depending on the determined or specific external damage and in consideration of a desired effect, for example desired properties of the hair after the treatment. The desired effect can be a user-defined effect or a desired condition of the hair. It can be helpful here to assign to each treatment agent one or more types of damage for which an application is possible and an effect which the treatment agent has on the corresponding type of damage. Thus, a simple comparison of the type of damage and the desired effect can be used to determine the appropriate treatment agent.

Execution examples of the present disclosure are shown in the figures and are explained in detail below. The FIGS. were summarized above, and the summary is repeated below to simplify understanding. The FIGS. show:

FIG. 1 a schematic representation of an arrangement for detecting external damage to hair according to an execution example.

Figure 2:
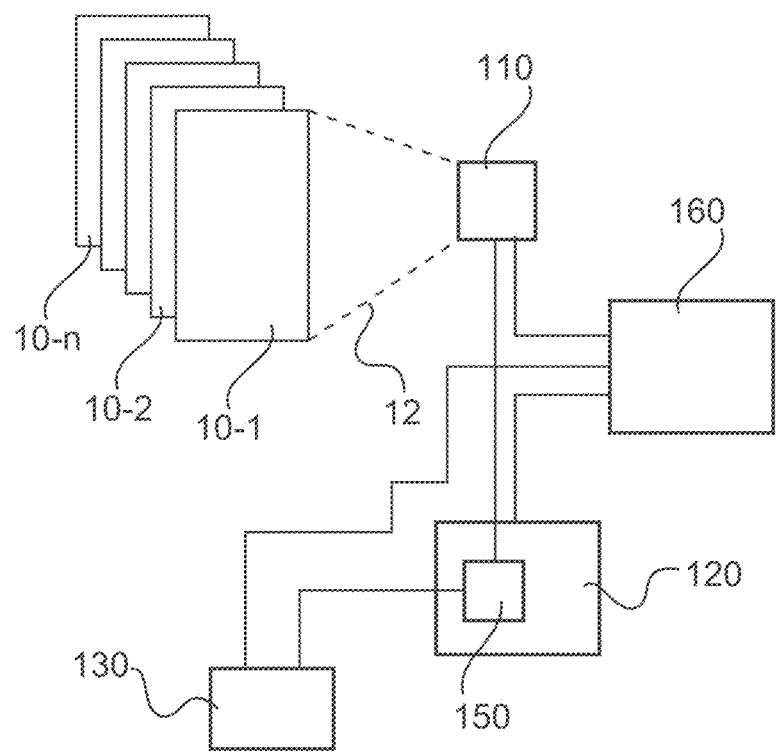
FIG. 2 is a schematic representation of an arrangement for detecting external damage to hair according to another execution example.

FIG. 2 a schematic representation of an arrangement for detecting external damage to hair according to another execution example.

Figure 3:
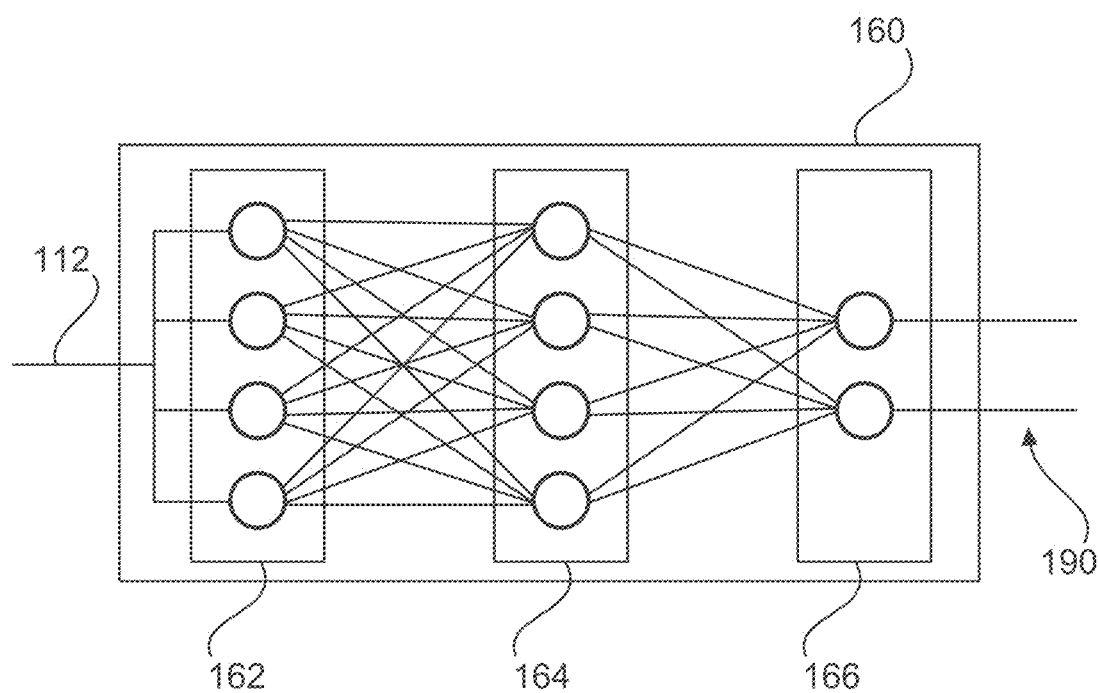
FIG. 3 is a schematic representation of a processing unit of an arrangement according to a further execution example.

FIG. 3 a schematic representation of a processing unit of an arrangement according to a further execution example.

Figure 4:
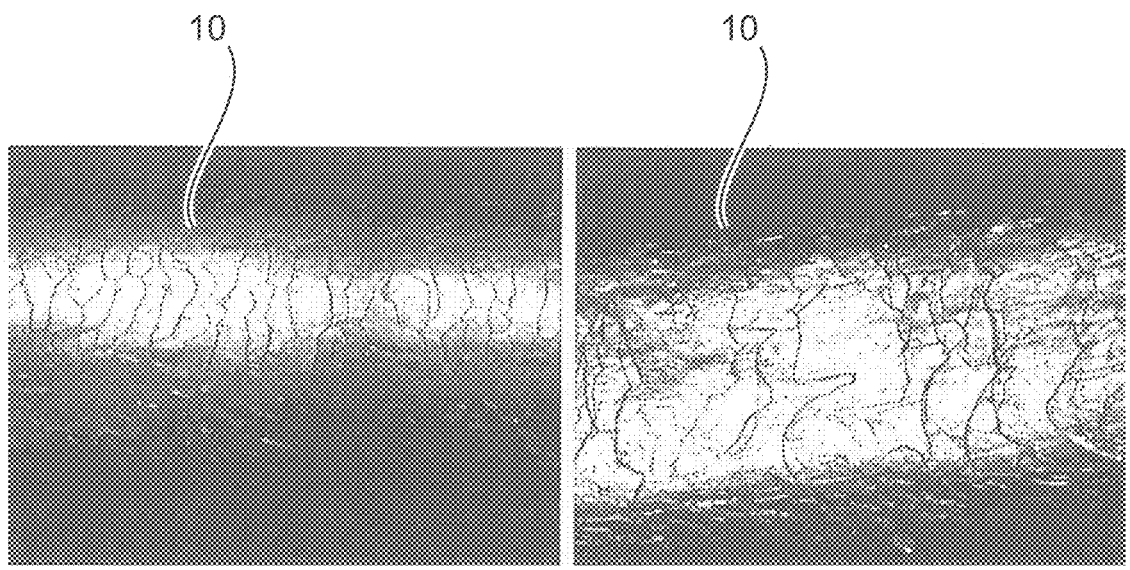
FIG. 4 is an exemplary photograph of a human hair.

FIG. 4 an exemplary photograph of a human hair.

Figure 5:
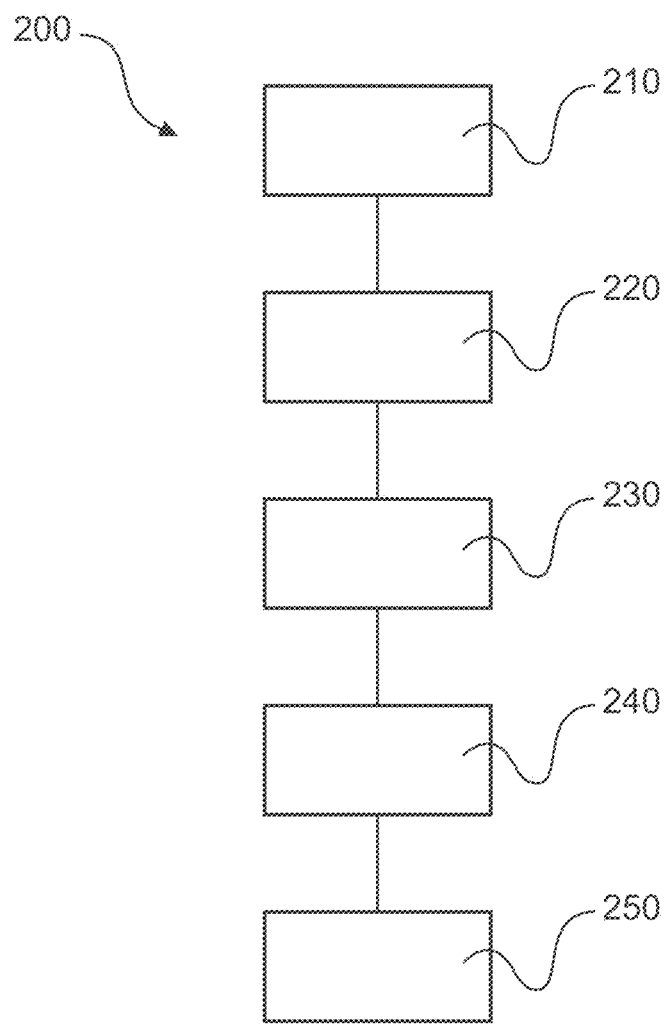
FIG. 5 is a schematic representation of steps of a process according to an execution example.

FIG. 5 a schematic representation of steps of a process according to an execution example.

In the following detailed description, reference is made to the attached drawings which form part of the present application and which, for illustrative purposes, show specific embodiments in which the present disclosure can be exercised. It is understood that other embodiments may be used and structural or functional or logical modifications may be made without departing from the scope of protection of the present disclosure. In this respect, directional terminology such as "top", "bottom", "front", "back", "front", "rear", etc. is used with reference to the orientation of the figure(s) described. Since components of embodiments can be positioned in several different orientations, the terminology of directions is for illustrative purposes only and is in no way restrictive. It is understood that the characteristics of the various exemplary designs described herein may be combined, unless specifically stated otherwise. The following detailed description is therefore not to be understood in a restrictive sense and the scope of protection of the present disclosure is defined by the appended claims and equivalents thereof.

FIG. 1 shows an arrangement 100 to determine an external damage of a hair sample 10. An optical detection unit 110 is arranged to make an optical image or image recording of the hair sample 10 in the surface area 12 to be examined. This image acquisition forms the basis for further examination and is transferred to the processing unit 160 via the reading unit 150. The reading unit 150 can also read image recordings of hair samples from a data memory 130.

A data transmission link 111 connects the optical acquisition unit 110 with the reading unit 150. The reading unit 150 can be designed as an interface between processing unit 160 and optical acquisition unit 110 and can, for example, convert or adapt the data format of the image recordings and also provide a mechanical connection between processing unit 160 and optical acquisition unit. The data transmission path 111 can be wireless or wired.

The connection between the data memory 130 and the reading unit 150 can also be designed in the same way as the data transmission link 111.

The reading unit 150 supplies input data 112 to the processing unit 160. For example, input data 112 is image data in a digital format.

The Processing Unit 160 performs analysis steps based on the image data of the hair sample. These analysis steps may include a comparison with known patterns and/or an examination of the image data using artificial neural networks. These analysis steps make it possible to assign a damage (type and degree of damage) to the hair sample, either by comparison with known hair samples classified in damage groups or by using the artificial neural network configured with known and categorized hair samples.

Processing unit 160 supplies the damage as output value 190 to an evaluation unit 195. Based on the damage of the hair sample, the evaluation unit 195 determines a recommendation for the treatment of the hair, either with reference to treatment agents to be used (including an application note) or without treatment agents. For this purpose, the evaluation unit 195 accesses information in a treatment agent data memory 197. The evaluation unit 195 is connected to the treatment agent data memory 197 via a data network 196. The data network 196 can enable unidirectional or bidirectional data exchange via a wired, wireless, or mixed connection.

The treatment agent data memory 197 can be spatially separated from the evaluation unit 195. For example, treatment agent data memory 197 is arranged in such a way that many arrangements 100 can access treatment agent data memory 197. This enables the treatment agent data memory 197 to be filled at a central location with information about treatment agents and/or treatment instructions. This information and treatment instructions can be revised and adapted independently of the requesting orders. In this way, current information can be supplied to requesting arrangements 100 or evaluation units 195.

FIG. 2 shows an example of how the Processing Unit 160 is prepared and/or configured for machine detection of external damage to hair samples. A variety of hair samples 10-1, 10-2, . . . , 10-n are acquired by the optical acquisition unit 110 and delivered as image data to the processing unit 160. Each individual image is also provided to a classification unit 120, whereby the reading unit 150 can serve as an interface between the optical acquisition unit 120 and the classification unit 120.

Using the Classification Unit 120, damage is assigned to each individual image acquisition of a hair sample, for example by a human operator. For example, degrees of damage are recorded as individual values on a scale for predefined types of damage. However, it is also conceivable that only a single value is recorded for a hair sample, which does not distinguish between types of damage, but describes the overall condition.

The image data can alternatively or additionally be read in from a data memory 130 and fed into the classification.

Based on the same approach, an artificial neural network can also be configured. Image data and associated damages are fed to the artificial neural network. After configuration, the artificial neural network can assign a damage to unknown images. The neural network can output either a single value for the total damage or a value for different types of damage, depending on the configuration of the neural network.

A neural network can thus be used in an advantageous way to determine and indicate the external damage from an image recording of a hair sample. This can greatly reduce the effort required to determine the external damage of a hair sample. For example, an image can be taken at one location and transmitted via a communication network to the processing unit at another location, where the hair sample is examined, and the result is delivered. This process can be completed in a few seconds or minutes. Apart from the optical acquisition unit, which must be able to produce images at the required magnification and resolution, it is not necessary to move the processing unit spatially.

FIG. 3 shows a schematic representation of processing unit 160 as an artificial neural network with an input layer 162, an intermediate layer 164 (or hidden layer) and an output layer 166.

The image data 112 are fed to the input layer 162. Each layer contains several artificial neurons, each of which receives an input value via at least one connection and is connected on the output side to at least one neuron of the following (further right) layer. The artificial neural network can contain a multitude of intermediate layers 164. The output value 190 can contain several single signals from several neurons of the output layer 166, where for example each single signal indicates a value. For example, a neuron of the initial layer can be assigned to a damage type and its value indicates the corresponding degree of damage.

FIG. 4 shows an example of an enlarged image of a hair, whereby the individual scales of the cuticle are visible. The left image shows an image with even distances between the edges of the scales, whereas in the right image these distances are uneven and indicate external damage to the hair. In addition to edge distances, other parameters can be used to determine the damage, such as whether the edges are round or frayed, whether the scales are attached or protruding at their edges, the length of exposed cuticle cells, the presence of holes and bubbles, surface roughness, deposits on the cuticle, or the visibility of the endocuticle.

FIG. 5 shows a schematic representation of process steps of a procedure 200 to determine external damages of a hair according to an execution example. Step 220 is intended to receive optical characteristics of hair. In a further step 230, the surface properties of the hair are determined based on the optical characteristics. Subsequently, in a following step 240 a damage of the surface properties is determined by employing a pattern recognition algorithm that is based on predetermined damages containing at least one damage type and an associated damage degree. In a fourth step 250 the output of the damage occurs.

As an introductory step 210, it can be a part of the procedure to configure the pattern recognition algorithm based on many hairs with different damage, whereby a damage is queried and assigned for each individual hair.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An arrangement for determining external damage to hair, the arrangement comprising:
   a reading unit, which is designed to obtain optical features of hair and wherein the reading unit is adapted to obtain the optical features from an optical detection unit;
   a processing unit, which is designed to receive the optical features from the reading unit and to determine surface properties of the hair from the optical features;
   wherein the processing unit implements a pattern recognition algorithm to determine the surface properties of the hair including a shape of a cuticle cell of the hair, a protrusion of the cuticle cell of the hair and a visibility of an endocuticle, and is adapted to assign, by employing the pattern recognition algorithm, the surface properties to a predetermined damage including a damage type and an associated damage level and to output the damage type and the damage level to an evaluation unit, wherein the pattern recognition algorithm is an artificial neural network comprising an input layer, at least one hidden layer and an output layer; and
   the evaluation unit for determining a treatment agent in response to a comparison of the damage type and the damage level with a predetermined damage type and a predetermined damage level.

2. The arrangement according to claim 1, where the processing unit is designed to output the damage based on the surface properties.

3. The arrangement according to claim 1,
   wherein the processing unit is adapted to operate the pattern recognition algorithm in a configuration mode; and
   wherein the processing unit is adapted to apply optical characteristics of a plurality of hairs with different damage to the pattern recognition algorithm in a configuration mode and to interrogate and assign damage for each individual hair of the plurality of hairs with different damage and its optical characteristics.

4. The arrangement according to claim 1, wherein the optical detection unit is a microscope having a magnification of at least about 100 times.

5. The arrangement according to claim 1, wherein the reading unit is designed to obtain the optical features from image recordings of hair, from a digital data memory, or a combination thereof.

6. The arrangement according to claim 1,
   wherein the evaluation unit is designed to compare characteristics of treatment agents for the treatment of hair with the damage to the hair, and to determine an effect of the treatment agents on the hair taking into account the damage to the hair.

7. The arrangement according to claim 6,
   wherein the evaluation unit is adapted to receive from a treatment agent data memory indications for the treatment of hair according to the damage to the hair and to output the indications received.

8. The arrangement according to claim 7,
   wherein the evaluation unit is adapted to query information from a user and to take this information into account when outputting the indications received from the treatment agent data memory in order to obtain from the treatment agent data memory characteristics of treatment agents for treating hair in accordance with the queried information from the user.

9. The arrangement according to claim 6,
   wherein the evaluation unit is designed to output information about a treatment agent, wherein the output information comprises one or more of a product name, information concerning ingredients of a treatment agent, a composition of a treatment agent, and application instructions for the treatment of hair.

10. The arrangement according to claim 6,
    wherein the evaluation unit is adapted to receive an input from a user after features of a treatment agent and/or application instructions have been output and to initiate an action concerning the output treatment agent and/or the output application instructions based on this input.

11. The arrangement according to claim 1, wherein the optical detection unit is a microscope having a magnification of at least about 500 times.

12. The arrangement according to claim 1, wherein the optical detection unit is a microscope having a magnification of at least about 1,000 times.

13. The arrangement according to claim 1, wherein the optical detection unit is a microscope having a magnification of at least about 2,000 times.

* * * * *